US006783496B2

(12) United States Patent
Hao et al.

(10) Patent No.: US 6,783,496 B2
(45) Date of Patent: Aug. 31, 2004

(54) METHOD AND APPARATUS FOR IMPROVING CONTRAST-TO-TISSUE RATIO IN ULTRASOUND CONTRAST IMAGING WITH SUBHARMONIC IMAGING

(75) Inventors: Xiaohui Hao, Waukesha, WI (US); Richard Yun Chiao, Menomonee Falls, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/286,547

(22) Filed: Nov. 1, 2002

(65) Prior Publication Data

US 2004/0087858 A1 May 6, 2004

(51) Int. Cl.[7] .................................................. A61B 8/14
(52) U.S. Cl. ...................................................... 600/458
(58) Field of Search .......................... 600/437, 440–471; 73/602, 625, 626; 128/916; 367/7, 11, 130, 138

(56) References Cited

U.S. PATENT DOCUMENTS

| | | | |
|---|---|---|---|
| 5,410,516 A | 4/1995 | Uhlendorf et al. | 367/7 |
| 5,632,277 A | 5/1997 | Chapman et al. | 128/660.07 |
| 5,678,553 A | 10/1997 | Uhlendorf et al. | 128/662.02 |
| 5,706,819 A | 1/1998 | Hwang et al. | 128/662.02 |
| 5,724,976 A | 3/1998 | Mine et al. | 178/662.03 |
| 5,733,527 A | 3/1998 | Schutt et al. | 424/9.52 |
| 6,117,082 A | 9/2000 | Bradley et al. | 600/447 |
| 6,186,949 B1 * | 2/2001 | Hatfield et al. | 600/443 |
| 6,371,914 B1 | 4/2002 | Arditi | 600/443 |

OTHER PUBLICATIONS

Cheri X. Deng, et al., "A Review of Physical Phenomena Associated With Ultrasonic Contrast Agents and Illustrative Clinical Applications," Ultrasound in Medicine and Biology, vol. 28, No. 3, pp. 227–286, 2002.

David Hope Simpson et. al, "Pulse Inversion Doppler: Anew Method for Detecting Nonlinear Echoes from Microbubble Contrast Agents", IEEE Transactions on Ultrasonics, Ferroelectrics, and Frequency Control, vol. 46, No. 2, Mar. 1999, pp. 372–382.

Chang PH et. al, "Second Harmonic Imaging and Harmonic Doppler Measurements with Albunex", IEEE Transactions on Ultrasonics, Ferroelectrics, and Frequency Control, vol. 42, No. 6, Nov. 1995, pp 1020–1027.

James E. Chomas et. al, "Subharmonic Phase–Inversion for Tumor Perfusion Estimation", 2001 IEEE Ultrasonic Symposium.

P. M. Shankar et. al, "Advantage of Subharmonic Over Second Harmonic Backscatter for Contrast–to–Tissue Echo Enhancement", Ultrasound in Medicine and Biology, vol. 24, No. 3, 1998, pp. 395–399.

* cited by examiner

*Primary Examiner*—Ali M Imam
(74) *Attorney, Agent, or Firm*—McAndrews, Held & Malloy, Ltd.; Peter J. Vogel; Michael A. Dellapenna

(57) ABSTRACT

The contrast-to-tissue ratio is improved while imaging contrast infused tissue. A subject is infused with contrast medium having microbubbles at a fundamental frequency. First and second transmit pulses are transmitted into the subject. The first and second transmit pulses each comprise first, or basic, and second, or seed, signals. The basic signal has a frequency based on the fundamental frequency and the seed signal has a subharmonic frequency based on the frequency of the basic signal. The first and second transmit pulses are phase inverted with respect to each other. Received echoes from first and second transmit pulses are filtered at a subharmonic or ultraharmonic frequency to remove tissue response and pass microbubble response.

24 Claims, 7 Drawing Sheets

Basic Signal at 6 MHz (0dB)    Transmit pulse #1(Positive)

Seed Signal at 3 MHz (-20dB)

Basic Signal at 6 MHz (0dB)    Transmit pulse #2 (Negative)

Seed Signal at 3 MHz (-20dB)

— bubble response
--- tissue response

— bubble response
--- tissue response

METHOD AND APPARATUS FOR IMPROVING CONTRAST-TO-TISSUE RATIO IN ULTRASOUND CONTRAST IMAGING WITH SUBHARMONIC IMAGING

BACKGROUND OF THE INVENTION

Certain embodiments of the present invention relate to ultrasound imaging of the human anatomy for the purpose of medical diagnosis. In particular, certain embodiments of the present invention relate to methods and apparatus for improving the ratio of contrast signals to tissue signals in ultrasound contrast imaging.

Contrast agents may be used with ultrasound imaging to enhance the clinical evaluation of blood flow and perfusion, which is the circulation of blood to an organ or tissue. The contrast agents comprise microbubbles which are typically 1–10 um in size. When injected into a patient's blood, the contrast microbubbles generate nonlinear signals and increase the ultrasound echo strength in comparison to the echo strength of blood without contrast. Tissue also generates nonlinear signals, but the nonlinear tissue signals are generally weaker than the nonlinear contrast signals.

In order to visualize blood flow or perfusion of tissue, the tissue echo strength must be significantly reduced relative to the contrast echo strength. One way to suppress the tissue signal is to image second or high harmonics of the nonlinear signals generated by the microbubbles. In basic harmonic imaging, a narrowband signal is transmitted at a frequency, $f_0$. In U.S. Pat. Nos. 5,724,979 and 5,733,527, the returned echoes are band pass filtered at $2f_0$ in order to image a second harmonic signal generated by the microbubbles and tissue. Alternatively, in U.S. Pat. Nos. 5,632,277, 5,706,819, and 6,3719,914, pulse inversion permits overlap of the fundamental and harmonic bands for better spatial resolution by using two phase inverted transmit pulses to cancel the fundamental (linear) component which leaves the nonlinear components to be imaged.

For each of the aforementioned conventional methods, the ratio of contrast to tissue signal strength is still insufficient for imaging tissue perfusion. One method to improve the contrast-to-tissue ratio (CTR) is to reduce the transmit mechanical index (MI), because the nonlinear signal of tissue falls faster than the nonlinear signal of contrast as the MI decreases. This method, however, experiences signal-to-noise ratio (SNR) limitations.

Compared to techniques which use second or high harmonics, subharmonic imaging has the advantage that tissue does not produce significant subharmonic content, and thus a high CTR can be maintained. (see U.S. Pat. No. 6,117,082; James Chomas et al., "Subharmonic Phase-Inversion for Tumor Perfusion Estimation"; P. M. Shankar et al., "Advantage of Subharmonic Over Second Harmonic Backscatter for Contrast-to-Tissue Echo Enhancement") Subharmonic imaging involves transmitting a pulse at a fundamental frequency, $f_0$, and filtering the received echoes to reject echoes at $f_0$, while receiving echoes at a subharmonic frequency of $f_0$, e.g. $f_0/2$, $f_0/3$, and the like. However, the subharmonic signal level is generally much lower than the second harmonic and fundamental signal. Another problem experienced while generating the subharmonic response is that a pressure threshold exists which may be too high for low MI real-time perfusion imaging.

Subharmonic generation is a positive feed back loop. In U.S. Pat. No. 6,117,082, a seed signal at a subharmonic frequency is introduced to induce the positive feed back of the subharmonic signal generation during the pulsing time. To avoid tissue signal generated by the seed signal, the seed signal is put almost 40 dB down compared to the fundamental signal. The low amplitude of the seed signal limits the speed for generating a high level subharmonic signal. Thus, high pressure and a long transmit pulse are needed to generate a strong subharmonic signal.

Recently, a phase inverted subharmonic imaging method was developed to further enhance the CTR. It was found that the threshold to generate subharmonic vibration could be low when the transmit frequency is at two times the microbubble resonance frequency. (James Chomas et al., "Subharmonic Phase-Inversion for Tumor Perfusion Estimation"). However, a seed subharmonic signal is not employed, so a high pressure is still needed to generate enough subharmonic signal for imaging.

For many contrast applications, and especially for perfusion imaging, bubble destruction has to be avoided. Contrast microbubbles are destroyed by high-MI ultrasound pulses, therefore, low-MI pulses are desired in order to not destroy contrast agents and in order to maintain a longer duration over which the contrast agents may be imaged.

Therefore, a need exists for a method to perform ultrasound imaging using contrast which generates a strong subharmonic signal and which improves the ratio of contrast echo signals to tissue echo signals, while not destroying the contrast microbubbles for continued imaging of microbubbles. It is an object of certain embodiments of the present invention to meet these needs and other objectives that will become apparent from the description and drawings set forth below.

BRIEF SUMMARY OF THE INVENTION

A method for improving contrast-to-tissue ratio while imaging contrast infused tissue and blood vessels is provided. The method includes infusing a subject with contrast medium having microbubbles having a fundamental frequency. A first transmit pulse comprising first and second signals is transmitted into the subject. The first signal has a first frequency based on the fundamental frequency and the second signal has a second frequency based on the first frequency and is lower than the first frequency. A second transmit pulse comprising third and fourth signals having the first and second frequencies, respectively, is transmitted into the subject. The third and fourth signals are phase inverted with respect to the first and second signals.

A method of imaging a patient using diagnostic ultrasound is provided including generating first and second signals having first and second frequencies, respectively. The second frequency is a subharmonic frequency with respect to the first frequency. The method further includes combining the first and second signals to create a first transmit pulse. Third and fourth signals are generated with the first and second frequencies, respectively, and the third and fourth signals are phase inverted with respect to the first and second signals. The third and fourth signals are combined to create a second transmit pulse.

A system for improving a contrast-to-tissue ratio while imaging contrast infused tissue and blood vessels is provided. The system includes a seeded waveform generator generating first and second transmit pulses comprising basic and seed signals. The basic signal has a first frequency and the seed signal has a second frequency which is a subharmonic frequency of the first frequency. The first and second transmit pulses are phase inverted with respect to each other. The system further includes a transmitter transmitting the first and second transmit pulses into a patient having tissue and blood vessels infused with contrast agent comprising microbubbles. A receiver receives first and second sets of echoes based on the first and second transmit pulses, respectively. A filter being centered at a frequency based on the second frequency filters the first and second sets of echoes to create filtered signals representing a response from the microbubbles.

Figure 1:
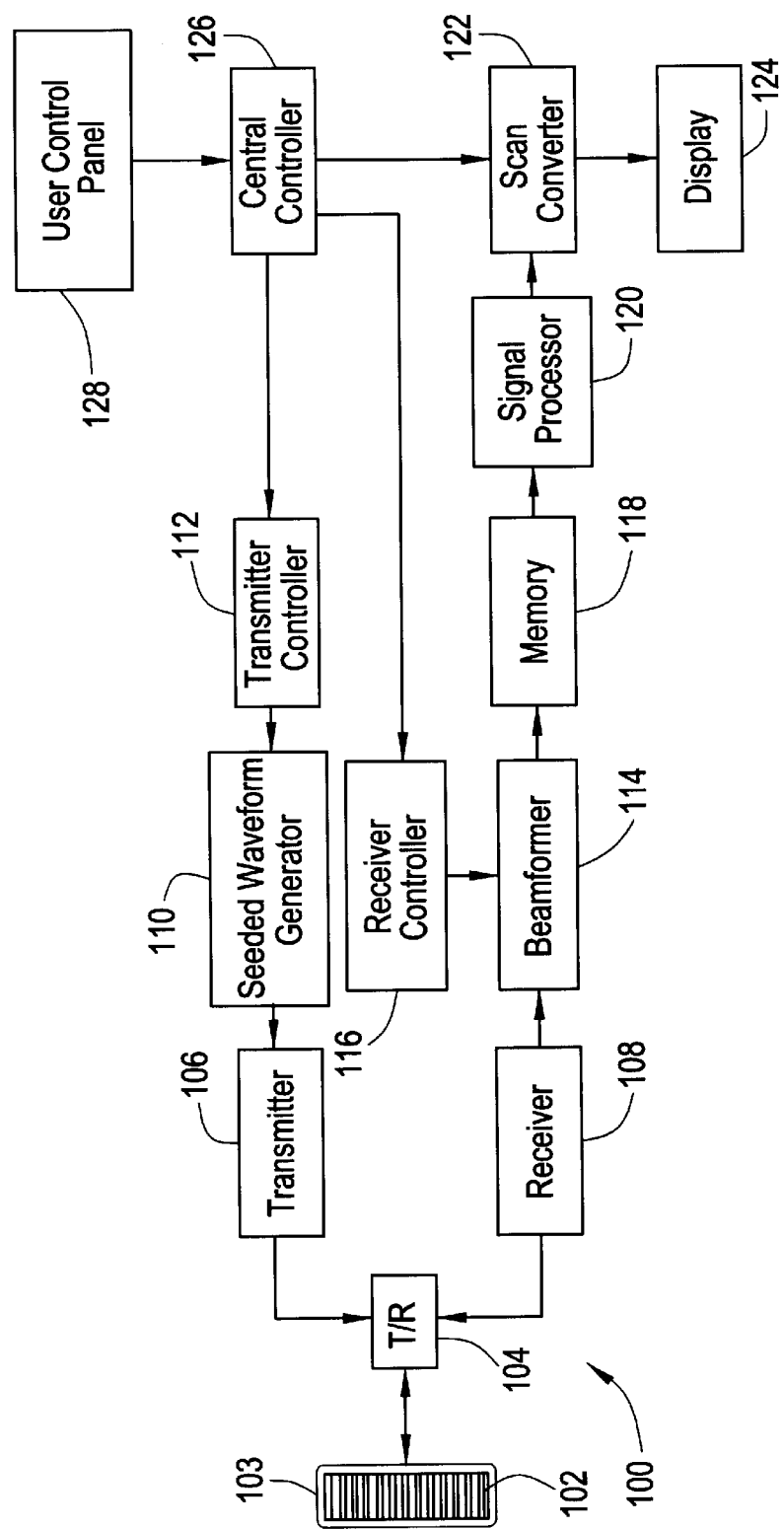
FIG. 1 illustrates a block diagram of an ultrasonic diagnostic imaging system formed in accordance with an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

FIG. 1 illustrates a block diagram of an ultrasonic diagnostic imaging system 100 formed in accordance with an embodiment of the present invention. The system 100 includes a transducer array 102 contained within an ultrasonic probe 103. The transducer array 102 is coupled via a transmit/receive switch 104 to a transmitter 106 and a receiver 108. The transmitter 106 drives the transducer array 102 to fire pulses, or emit pulsed ultrasonic signals, into an object or body. A seeded waveform generator 110 generates seeded waveforms which are further discussed below. Seeded waveforms may be transmitted sequentially in time, along the same spatial line, by the transmitter 106, which is controlled by transmitter controller 112.

The ultrasonic signals are backscattered from structures in the body, like blood cells, muscular tissue or contrast microbubbles, to produce echoes which are detected by the transducer array 102. The echoes from each transmit pulse are received sequentially by receiver 108. The received echoes are passed through a beamformer 114, which performs beamforming and filtering operations and is controlled by a receiver controller 116. The received signals are then stored in memory 118. A central controller 126 coordinates higher-level functions of the ultrasound imaging system, such as user inputs from a user control panel 128, display of data on a display 124, and the like.

Figure 2:
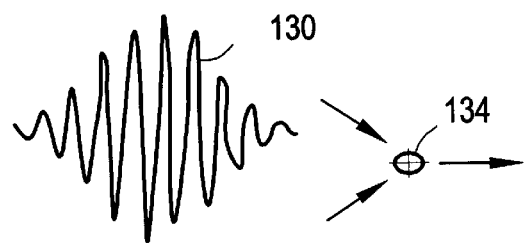
FIG. 2 illustrates how two consecutive seeded transmit pulses may be formed in accordance with an embodiment of the present invention.
Figure 2:
Figure 2:
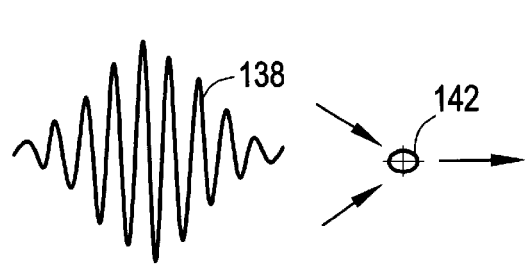
Figure 2:
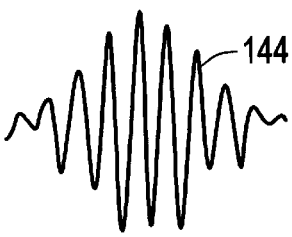
Figure 2:

FIG. 2 illustrates how two consecutive seeded transmit pulses may be formed. The seeded waveform generator 110 generates a first signal, basic signal 130, and a second signal, seed signal 132. The basic signal 130 and seed signal 132 are then combined by a combining operation 134 within the seeded waveform generator 110 to produce a seeded transmit pulse 136. The combining operation may comprise adding, subtracting, coherent synthesizing, or other functions. The basic signal 130 may have a basic frequency $2f_0$, wherein $f_0$ is the resonance frequency of the contrast microbubbles. The seed signal 132 is at a subharmonic frequency of $2f_0$, such as $f_0$, $2f_0/3$, and the like. Alternatively, the basic signal 130 may have a basic frequency $f_0$, while the seed signal 132 has a subharmonic frequency of $f_0$, such as $f_0/2$. In the example of FIG. 2, the basic signal 130 has a transmit frequency of 6 Mhz, and seed signal 132 has a transmit frequency of 3 MHz.

As described in the background, subharmonic generation is a positive feed back response. Here, seed signal 132 is introduced to start the positive feed back loop of subharmonic generation. The amplitude of the seed signal 132 is between approximately –10 dB to approximately –30 dB with respect to the basic signal 130. At the amplitude level used here, the subharmonic signal can be generated to high amplitude in a short pulse duration time such as 4 or 6 cycles with 6 MHz, for example, that makes it practical to be applied in the current commercial probes. Also, since when the microbubble is insonated with 2 times the microbubble's resonance frequency, the threshold level for subharmonic generation could be very low, thus low MI value can be easily reached with good subharmonic response.

The aforementioned process is repeated to generate phase inverted basic signal 138 and phase inverted seed signal 140. The phase inverted basic signal 138 and phase inverted seed signal 140 are combined by a combining operation 142 to form phase inverted seeded transmit pulse 144. The combining operation 142 may be the same operation and/or structure as the combining operation 134.

Basic signal 138 is a phase inverted version of basic signal 130. Seed signal 140 is a phase inverted version of seed signal 132. Thus, it should be recognized that the phase relation between the basic signal 130 and seed signal 132 is the same as the phase relation between the phase inverted basic signal 138 and phase inverted seed signal 140. In other words, the phase inverted seeded transmit pulse 144 of the second firing is phase inverted, or negative, with respect to the seeded transmit pulse 136 of the first firing, which is positive. Alternatively, the phase inverted seeded transmit pulse 144 may be generated by phase inverting the seeded transmit pulse 136.

Returning to FIG. 1, after the two phase inverted received signals are processed and stored in memory 118, the two phase inverted received signals are integrated together with coherent synthesizing by the signal processor 120. The signal processor 120 then filters the integrated signals at the subharmonic frequency band, such as $f_0$ or at an ultraharmonic frequency band, such as $4f_0/3$. The resultant processed signals are envelope detected and log compressed, then sent by the signal processor 120 to the scan converter 122. The processed signals are then displayed by the display 124.

Figure 3:
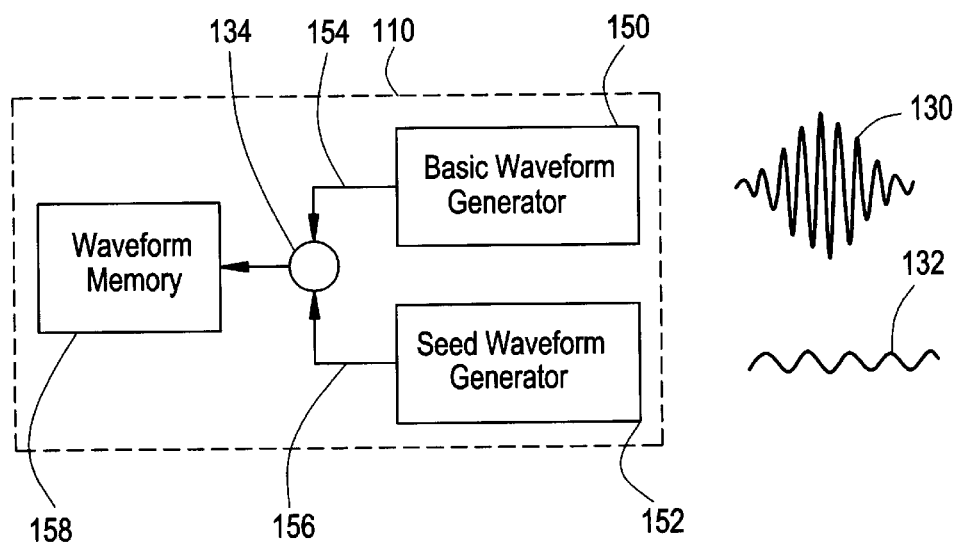
FIG. 3 illustrates the seeded waveform generator of FIG. 1 formed in accordance with an embodiment of the present invention.

FIG. 3 illustrates the seeded waveform generator 110 of FIG. 1. The seeded waveform generator 110 includes a basic waveform generator 150 and seed waveform generator 152. The basic waveform generator 150 generates the basic signal 130 at a first frequency, and the seed waveform generator 152 generates the seed signal 132 at a subharmonic frequency of the first frequency. The basic signal 130 and seed signal 132 are shown for reference. The basic waveform generator 150 outputs the basic signal 130 at output 154 and the seed waveform generator 152 outputs the seed signal 132 at output 156. The basic signal 130 and seed signal 132 are then combined to form the seeded transmit pulse 136 (FIG. 2) by the combining operation 134. The seeded transmit pulse 136 is then stored in a waveform memory 158 until being transmitted. The phase inverted version of the signal, such as phase inverted basic signal 138 and phase inverted seed signal 140 (FIG. 2), are generated, combined and stored in the same manner to produce phase inverted seeded transmit pulse 144.

Figure 4:
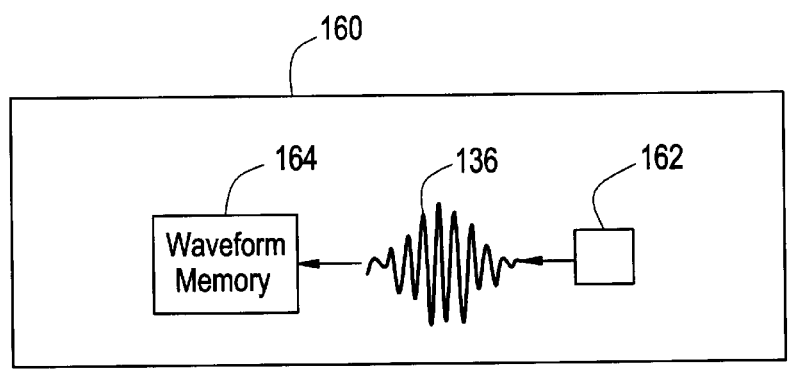
FIG. 4 illustrates an alternative seeded waveform generator formed in accordance with an embodiment of the present invention.

FIG. 4 illustrates an alternative seeded waveform generator 160. In FIG. 4, a single waveform generator 162 generates the seeded transmit pulse 136 by using predefined parameters stored, for example, by the central controller 126, or parameters input through a user control panel 128. The seeded transmit pulse 136 is then saved in a waveform memory 164 until being transmitted. The phase inverted seeded transmit pulse 144 is generated in the same manner as the corresponding seeded transmit pulse 136. Therefore, a person of ordinary skill in the art would recognize that the seeded transmit pulse 136 and phase inverted seeded transmit pulse 144 may be generated using a number of different methods and/or apparatus, and thus should not be limited to the embodiments discussed herein. In addition, it should be understood that the phase, bandwidth and amplitude of the basic and seed signals 130 and 132, and the phase inverted basic and phase inverted seed signals 138 and 140 may be changed, and also the time the seed signal 132, 140 is merged into the basic signal 130, 138, respectively, may be changed for optimization of subharmonic signal generation.

Figure 5:
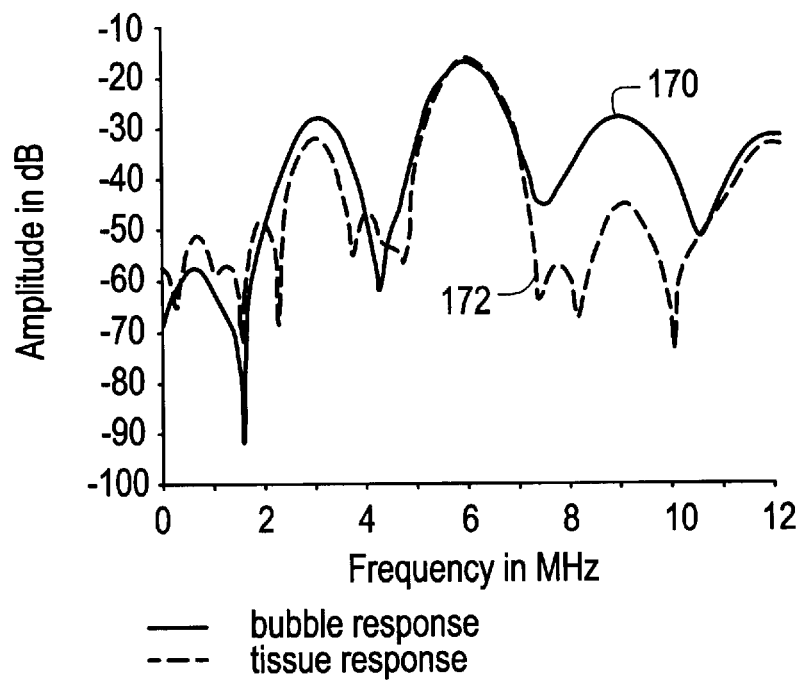
FIG. 5 illustrates a simulated power spectra of echoes received from the tissue and the contrast microbubbles when the seeded transmit waveform is transmitted.

FIG. 5 illustrates a simulated power spectra of echoes received from the tissue and the contrast microbubbles when the seeded transmit waveform 136 is transmitted. In FIG. 5, seeded transmit waveform 136 comprises the basic signal being transmitted at 6 MHz, $2f_0$, and the seed signal 132 being transmitted at 3 MHz, or $f_0$. The bubble concentration is modulated to make the total microbubble echoes have the same level response with the tissue at fundamental frequency $2f_0$. Line 170 illustrates the power spectrum of a set of echoes received by the receiver 108 from the contrast microbubbles. Line 172 illustrates the power spectrum of a set of echoes received by the receiver 108 from the tissue. The contrast microbubble response, line 170, has approximately the same level of response as the tissue response, line 172, at 6 MHz, or $2f_0$. Also, it can be seen that the linear response of the tissue is strong at the frequency of the seed signal $f_0$ (3 MHz), thus there is only a small difference between the bubble and tissue responses at the subharmonic frequency $f_0$. As a result, the CTR of the image is very low when imaging with the seeded transmit pulse 136 alone.

Figure 6:
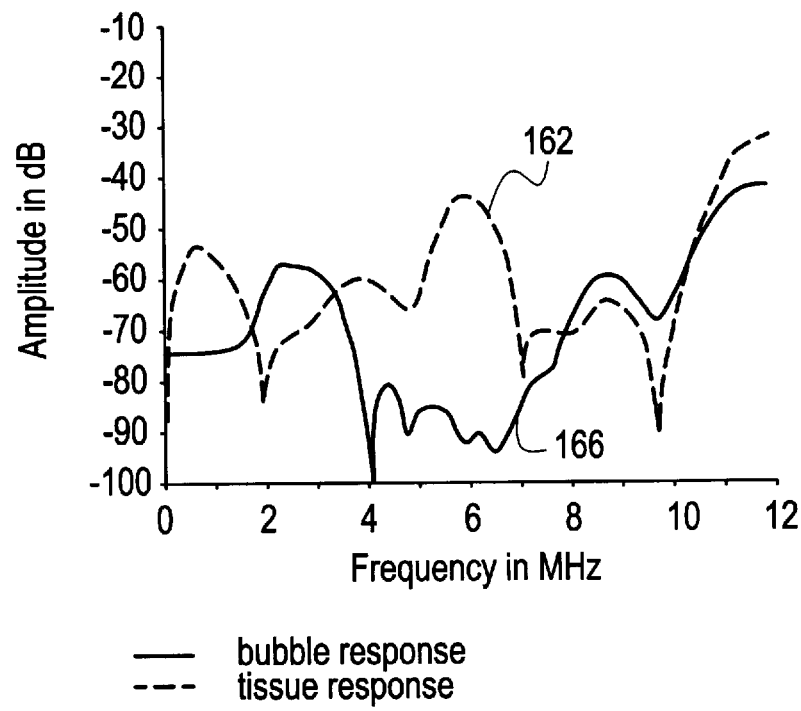
FIG. 6 illustrates a simulated power spectra of echoes received from the tissue and the contrast microbubbles when the basic signal and the phase inverted basic signal are transmitted.

FIG. 6 illustrates a simulated power spectra of echoes received from the tissue and the contrast microbubbles when the basic signal 130 and the phase inverted basic signal 138 are transmitted. In FIG. 6, the basic signal 130 and phase inverted basic signal 138 are transmitted at frequency $2f_0$, or 6 MHz, wherein $f_0$ is the resonant frequency of the contrast microbubbles. Line 166 illustrates the power spectrum of the combined set of echoes received by the receiver 108 from the contrast microbubbles insonated by basic signal 130 and phase inverted basic signal 138. Line 168 illustrates the power spectrum of the combined set of echoes received by the receiver 108 from the tissue insonated by basic signal 130 and phase inverted basic signal 138. The simulation was done with the transmit signals at the same amplitude level of the signal simulated in FIG. 5. It can be seen that at the subharmonic frequency band, which in this case is around 3 MHz, the CTR is also very low.

Figure 7:
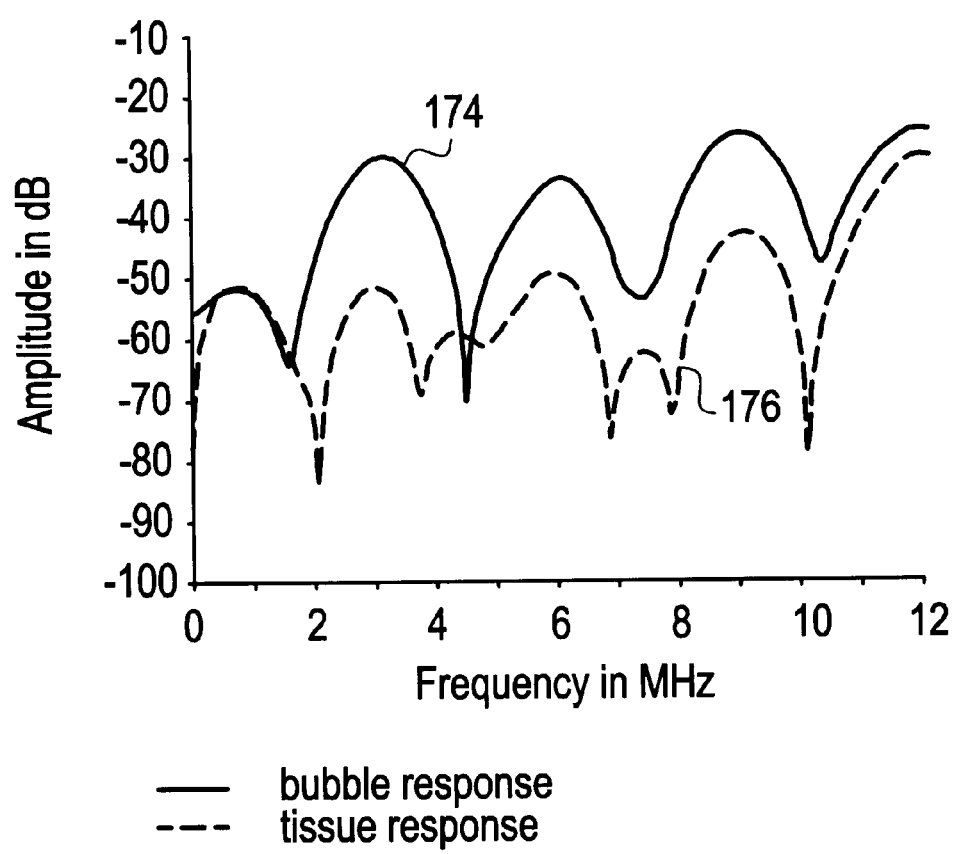
FIG. 7 illustrates a simulated power spectra of echoes received from tissue and contrast microbubbles when seeded transmit pulse and phase inverted seeded transmit pulse are transmitted in accordance with an embodiment of the present invention.

FIG. 7 illustrates a simulated power spectra of echoes received from tissue and contrast microbubbles when seeded transmit pulse 136 and phase inverted seeded transmit pulse 144 are both transmitted. Line 174 illustrates the power spectrum of the combined set of echoes received from the contrast microbubbles, and line 176 illustrates the power spectrum of the combined set of echoes received from the tissue. In simulation, the contrast microbubble concentration is the same as the contrast microbubble concentration employed in FIG. 6 and FIG. 5. The difference between the tissue signal (line 176) and the bubble signal (line 174) has been significantly improved in the subharmonic frequency band $f_0$, resulting in a much higher CTR compared to the result of the single firing of seeded transmit pulse 136 shown in FIG. 5 and phase-inversion firings with only basic signal 130 and phase inverted basic signal 138 shown in FIG. 6.

FIGS. 5, 6 and 7 illustrate that the seeded subharmonic phase inversion method employed in FIG. 7 improves the CTR in ultrasound contrast imaging. The −20 dB to −13 dB seeded signal level helps the positive feed back loop to start and reach a very high level, even saturation, within a short pulse duration time and with a low MI setting, while the phase inversion helps to eliminate the strong linear tissue signal generated by the seed signal inside the tissue. Additionally, the contrast imaging performance may be greatly improved when using high frequency probes (above or equal to 5 MHz) with low MI settings. As an example, the ability to image blood flow and regional micro-vascular perfusion in tissue is improved where high frequency probes are needed, such as the breast, prostrate, and thyroid.

Figure 8:
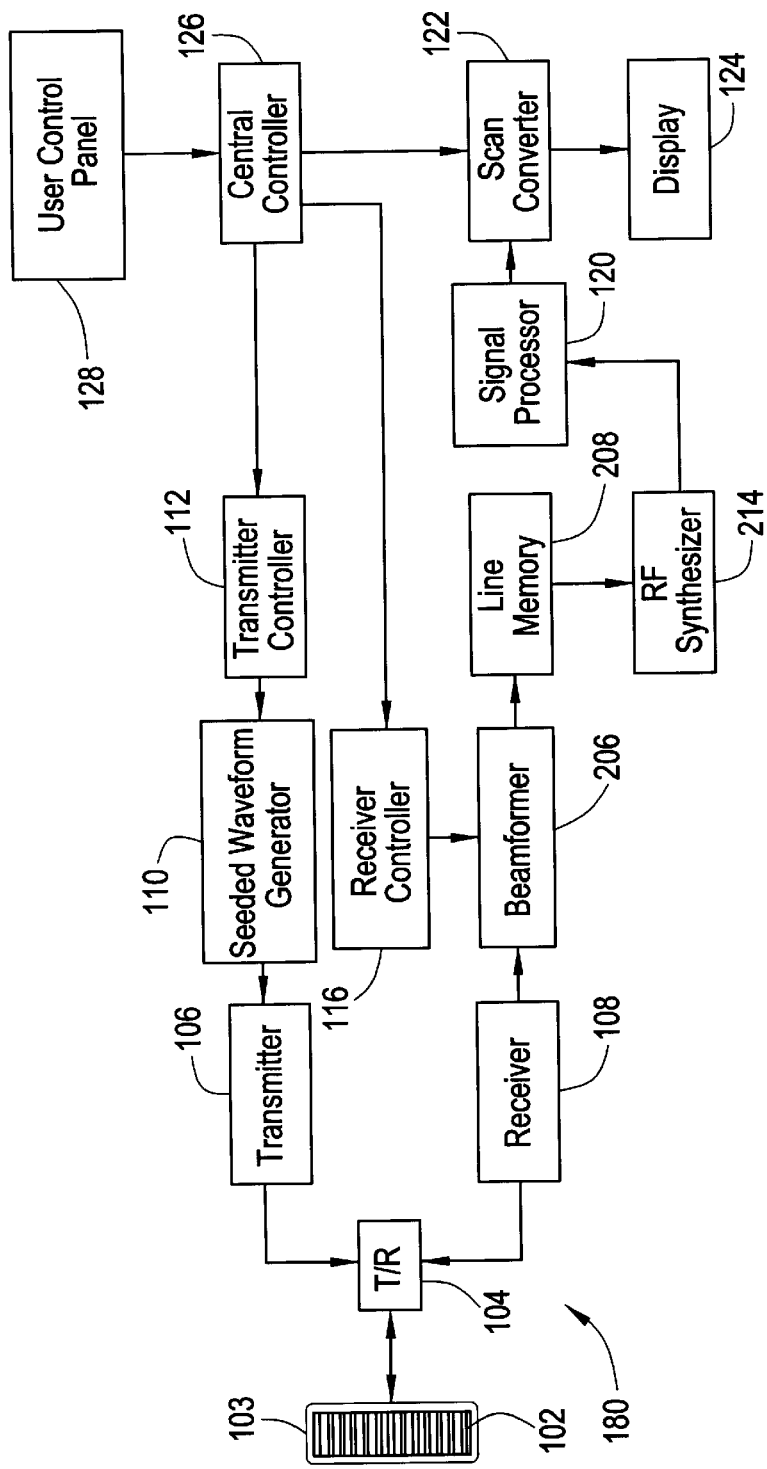
FIG. 8 illustrates a block diagram of a coherent beam forming ultrasonic diagnostic imaging system formed in accordance with an embodiment of the present invention.

FIG. 8 illustrates a block diagram of a coherent beam forming ultrasonic diagnostic imaging system 180 formed in accordance with an embodiment of the present invention. The system 180 utilizes some of the same components as the system 100, which are illustrated with the same reference numbers. By using coherent beamforming technology, the frame rate can be increased (e.g., doubled) when compared to the frame rate of system 100.

Figure 9:
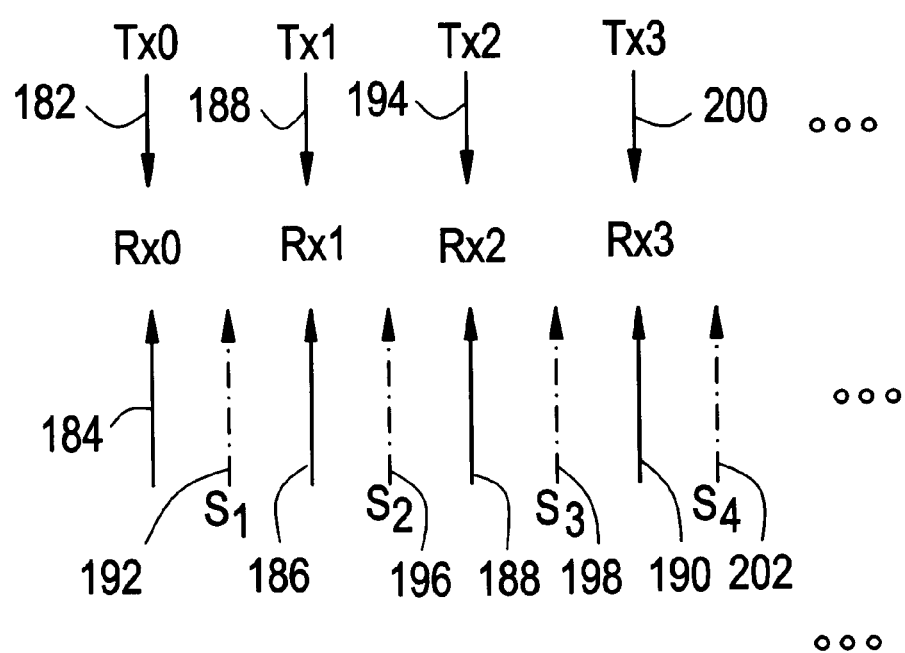
FIG. 9 illustrates how coherent beam forming may be implemented with seeded subharmonic phase inversion in accordance with an embodiment of the present invention.

FIG. 9 illustrates how coherent beam forming may be implemented with seeded subharmonic phase inversion. FIGS. 8 and 9 will be discussed together. In FIG. 8, the seeded waveform generator 110 generates the seeded transmit pulse 136 and phase inverted seeded transmit pulse 144 as previously discussed. In coherent beamforming system 180, instead of transmitting 136 and 144 sequentially in time along the same spatial line as in system 100, seeded pulse 136 is transmitted along line 182, Tx0, while seeded pulse 144 is transmitted along line 188, Tx1. Echoes from microbubbles insonated by seeded transmit pulse 136 will be received along the same spatial line as line 182 and echoes from microbubbles insonated by the phase inverted seeded transmit pulse 144 will be received along the same spatial line as line 188 shown in FIG. 9. This scan sequence will continue, transmitting seeded transmit pulse 136 along line 194, Tx2, receiving echoes along line 188, Rx2, transmitting phase inverted seeded transmit pulse 144 along line 200, Tx3, receiving echoes along line 190, Rx3, and so on, until an entire image is formed.

Echo signals received by receiver 108 will be beamformed by beamformer 206, then sent to line memory 208. An RF synthesizer 214 then coherently synthesizes neighboring received lines, resulting in a set of new synthetic lines SN 192, 196, 198, 202, in between the transmitting and receiving lines. The new synthetic lines SN 192, 196, 198, 202 are a combination of echoes from microbubbles insonated by seeded transmit pulse 136 and phase inverted seeded transmit pulse 144. Therefore, phase inversion is implemented in one frame scanning without two firings along the same spatial line. Thus, the frame rate can be doubled. The RF synthesizer 214 outputs the coherently synthesized phase inversion signals SN (N=1, 2, . . . ) to the signal processor 120. The signal processor 120 performs further filtering at the subharmonic or ultraharmonic band, then the signal is envelope detected and log compressed. The signal is then sent to the scan converter 122 and then to the display 124. The central controller 126 coordinates all higher-level functions of the system 180, similar to the central controller 126 of system 100.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for improving contrast-to-tissue ratio while imaging contrast infused tissue and blood vessels, said method comprising:

infusing a subject with contrast medium, said contrast medium comprising microbubbles having a fundamental frequency;

transmitting a first transmit pulse into the subject, said first transmit pulse comprising a first signal combined with a second signal, said first signal having a first frequency based on said fundamental frequency, said second signal having a second frequency based on said first frequency, said second frequency being lower than said first frequency; and transmitting a second transmit pulse into the subject, said second transmit pulse comprising a third signal having said first frequency combined with a fourth signal having said second frequency, said third and fourth signals being phase inverted with respect to said first and second signals.

2. The method of claim 1, further comprising:

receiving a first set of echoes based on said first transmit pulse;

receiving a second set of echoes based on said second transmit pulse; and filtering said first and second sets of echoes with a filter centered at a frequency based on said second frequency.

3. The method of claim 1, further comprising:

receiving first and second sets of echoes based on said first and second transmit pulses, respectively;

filtering, with a band pass filter centered at a frequency based on said second frequency, said first and second sets of echoes to create first and second sets of filtered echoes; and combining said first and second sets of filtered echoes using one of coherent summing and coherent subtraction to create an output representing a response from said microbubbles.

4. The method of claim 1, said first frequency being equal to said fundamental frequency.

5. The method of claim 1, said first frequency being equal to an integer times said fundamental frequency, said integer being at least 2.

6. The method of claim 1, said second frequency being a subharmonic frequency with respect to said first frequency.

7. The method of claim 1, further comprising:

transmitting said first and second transmit pulses along adjacent transmit lines;

receiving along adjacent receive lines first and second sets of echoes based on said first and second transmit pulses; and coherently synthesizing said first and second sets of echoes received along said adjacent receive lines to create a combination of echoes.

8. The method of claim 1, said second signal having an amplitude being not less than −30 dB with respect to said first signal.

9. The method of claim 1, wherein said first and second transmit pulses are transmitted simultaneously.

10. The method of claim 1, wherein said first and second transmit pulses are transmitted sequentially in time.

11. The method of claim 1, said first and second signals having a first phase relation and said third and fourth signals having a second phase relation, said first and second phase relations being the same.

12. The method of claim 1, further comprising:

receiving first and second sets of echoes based on said first and second transmit pulses, respectively;

combining said first and second sets of echoes using one of coherent summation and coherent subtraction to create an output representing a response from said microbubbles; and filtering, with a band pass filter centered at a frequency based on said second frequency.

13. A method for imaging a patient using diagnostic ultrasound, comprising:

generating first and second signals having first and second frequencies, respectively, said second frequency being a subharmonic frequency with respect to said first frequency;

combining said first and second signals to create a first transmit pulse;

generating third and fourth signals with said first and second frequencies, respectively, said third and fourth signals being phase inverted with respect to said first and second signals; and combining said third and fourth signals to create a second transmit pulse.

14. The method of claim 13, further comprising infusing the patient with a contrast agent comprising microbubbles, said microbubbles having a fundamental frequency, said first frequency being based on said fundamental frequency.

15. The method of claim 13, further comprising:

transmitting said first and second transmit pulses into the patient;

receiving first and second sets of echoes based on said first and second transmit pulses; and filtering said first and second sets of echoes with a filter centered at a subharmonic frequency.

16. The method of claim 13, said first signal having a first amplitude, said second signal having an amplitude within a range of 10 dB to 30 dB down with respect to said first amplitude.

17. The method of claim 13, said first and second signals having a first phase relation and said third and fourth signals having a second phase relation, said first and second phase relations being the same.

18. The method of claim 13, further comprising:

transmitting said first and second transmit pulses into the patient;

receiving first and second sets of echoes based on said first and second transmit pulses; and filtering said first and second sets of echoes with a filter centered at an ultraharmonic frequency based on said second frequency.

19. A system for improving a contrast-to-tissue ratio while imaging contrast infused tissue and blood vessels, the system comprising:

a seeded waveform generator generating first and second transmit pulses comprising basic and seed signals combined with one another for each of said first and second transmit pulses, said basic signal having a first frequency, said seed signal having a second frequency, said second frequency being a subharmonic frequency of said first frequency, said first and second transmit pulses being phase inverted with respect to each other;

a transmitter transmitting said first and second transmit pulses into a patient having tissue and blood vessels infused with contrast agent, said contrast agent comprising microbubbles;

a receiver receiving first and second sets of echoes based on said first and second transmit pulses, respectively; and a filter having said second frequency, said filter filtering said first and second sets of echoes to create filtered signals representing a response from said microbubbles.

20. The system of claim 19, said microbubbles having a fundamental frequency, said first frequency being based on said fundamental frequency.

21. The system of claim 19, said seeded waveform generator further comprising a combining operator combining said basic and seed signals to form said first and second transmit pulses.

22. The system of claim 19, said seeded waveform generator generating said basic and seed signals, said seed signal having an amplitude being within a range of 13 dB to 20 dB down with respect to said basic signal.

23. The system of claim 19, said microbubbles having a fundamental frequency, said second frequency being substantially the same as said fundamental frequency.

24. The system of claim 19, said transmitter transmitting said first and second pulses along adjacent spatial lines and said receiver receiving said first and second sets of echoes along said adjacent spatial lines, said system further comprising an RF synthesizer coherently synthesizing said first and second sets of echoes received by said receiver along said adjacent spatial lines to generate synthetic lines.

* * * * *